(12) United States Patent
Burke et al.

(10) Patent No.: US 10,959,763 B2
(45) Date of Patent: Mar. 30, 2021

(54) METHOD AND SYSTEM FOR THE REDUCTION AND FIXATION OF BONE SEGMENTS

(71) Applicants: Shawn Burke, Jacksonville, FL (US); Carson Quigley, Jacksonville, FL (US); Thomas Koett, Kolbingen (DE)

(72) Inventors: Shawn Burke, Jacksonville, FL (US); Carson Quigley, Jacksonville, FL (US); Thomas Koett, Kolbingen (DE)

(73) Assignee: KLS MARTIN, L.P., Jacksonville, FL (US)

(*) Notice: Subject to any disclaimer, the term of this patent is extended or adjusted under 35 U.S.C. 154(b) by 107 days.

(21) Appl. No.: 15/996,155

(22) Filed: Jun. 1, 2018

(65) Prior Publication Data

US 2018/0344369 A1 Dec. 6, 2018

Related U.S. Application Data

(60) Provisional application No. 62/513,656, filed on Jun. 1, 2017.

(51) Int. Cl.
| | |
|---|---|
| *A61B 17/80* | (2006.01) |
| *A61B 17/56* | (2006.01) |
| *A61B 17/16* | (2006.01) |
| *A61B 17/86* | (2006.01) |
| *A61B 17/88* | (2006.01) |

(Continued)

(52) U.S. Cl.
CPC ...... *A61B 17/8057* (2013.01); *A61B 17/1655* (2013.01); *A61B 17/8004* (2013.01); *A61B 17/808* (2013.01); *A61B 17/8019* (2013.01); *A61B 17/8076* (2013.01); *A61B 17/8605* (2013.01); *A61B 17/8615* (2013.01); *A61B 17/8888* (2013.01); *A61B 17/8891* (2013.01); *A61B 17/1728* (2013.01); *A61B 17/86* (2013.01); *A61B 2090/037* (2016.02)

(58) Field of Classification Search
CPC .............................................. A61F 17/80–8095
See application file for complete search history.

(56) References Cited

U.S. PATENT DOCUMENTS

| | | | | |
|---|---|---|---|---|
| 3,244,170 A | * | 4/1966 | McElvenny | ....... A61B 17/8019 606/71 |
| 4,119,092 A | * | 10/1978 | Gil | ..................... A61B 17/8004 606/96 |

(Continued)

*Primary Examiner* — Zade Coley
(74) *Attorney, Agent, or Firm* — Thomas C. Saitta

(57) ABSTRACT

A method and system for reducing and affixing two separated bone segments, the system having a bone plate with a pair of positioning slots, and a pair of elongated manipulating members with anchoring structures, the anchoring structures sized to pass through the positioning slots and for advancement into the bone segments. The bone plate is loosely mounted to the bone segments across the separation gap and a manipulating member is screwed into each bone segment through a positioning slot. The manipulating members are then used to reposition the bone segments by moving them together longitudinally within the slots. Fixation bone screws are inserted into the bone segments through screw receiving apertures to securely affix the bone plate to the repositioned bone segments. The manipulating members are then removed.

8 Claims, 4 Drawing Sheets

(51) Int. Cl.
  *A61B 17/17* (2006.01)
  *A61B 90/00* (2016.01)

(56) References Cited

U.S. PATENT DOCUMENTS

| | | | | |
|---|---|---|---|---|
| 4,929,247 A * | 5/1990 | Rayhack | ............ | A61B 17/8019 606/105 |
| 5,586,985 A | 12/1996 | Putman et al. | | |
| 6,299,616 B1 * | 10/2001 | Beger | .................. | A61B 17/862 606/86 R |
| 6,436,100 B1 * | 8/2002 | Berger | .................. | A61B 17/60 411/394 |
| 6,440,135 B2 | 8/2002 | Prbay et al. | | |
| 7,537,604 B2 | 5/2009 | Huebner | | |
| 7,704,257 B2 * | 4/2010 | Murner | ............ | A61B 17/8019 606/105 |
| 8,162,996 B2 * | 4/2012 | Schelling | ............ | A61B 17/8061 606/281 |
| 8,523,919 B2 * | 9/2013 | Huebner | ............ | A61B 17/1782 606/280 |
| 8,545,539 B2 | 10/2013 | Spencer | | |
| 8,763,499 B2 * | 7/2014 | Dahners | ............... | F16B 23/0084 81/451 |
| 9,011,507 B2 * | 4/2015 | Schelling | ............ | A61B 17/8042 606/324 |
| 2005/0085818 A1 | 4/2005 | Huebner | | |
| 2005/0277941 A1 * | 12/2005 | Trumble | ............ | A61B 17/8004 606/79 |
| 2007/0270850 A1 * | 11/2007 | Geissler | ................. | A61B 17/15 606/326 |
| 2010/0016900 A1 * | 1/2010 | Terres | ................ | A61B 17/8071 606/280 |
| 2011/0288595 A1 * | 11/2011 | Niederberger | ..... | A61B 17/8019 606/286 |

* cited by examiner

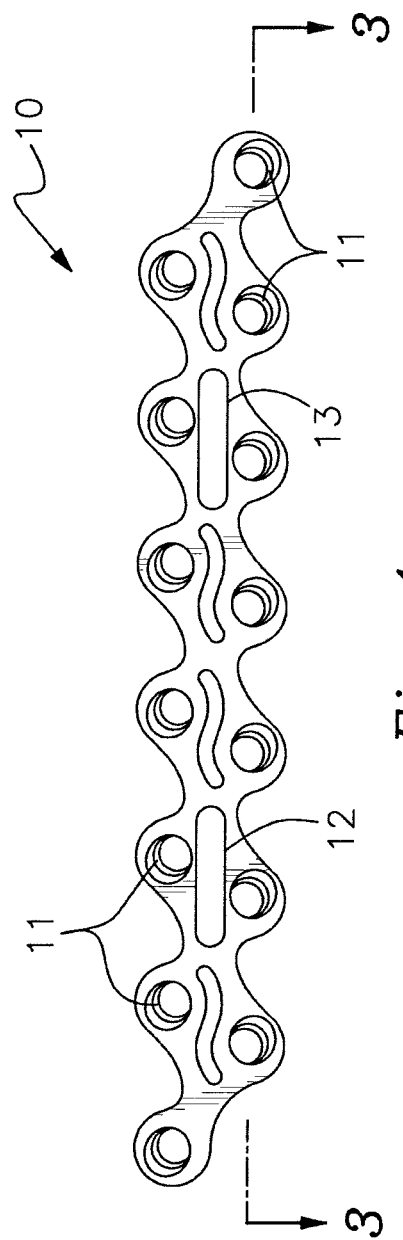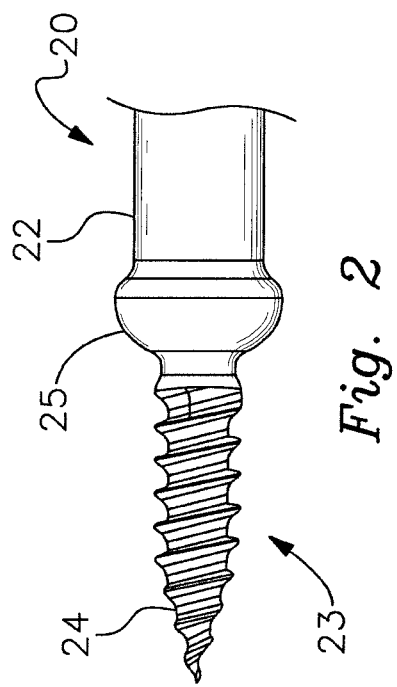

METHOD AND SYSTEM FOR THE REDUCTION AND FIXATION OF BONE SEGMENTS

This application claims the benefit of U.S. Provisional Patent Application Ser. No. 62/513,656, filed Jun. 1, 2017.

BACKGROUND OF THE INVENTION

This application relates generally to the field of methods and systems for the repair and fixation of bones that have been damaged, fractured or separated, and more particularly relates to such methods and systems facilitating movement of the bone segments for proper positioning and alignment prior to affixation with a bone plate.

The use of bone plates that are affixed with mechanical fasteners across junctions or gaps between bone segments is well known, the bone plates being sufficiently rigid to maintain the bone segments in the reduced, fixed relationship. The bone segments typically must be manipulated into the proper relationship, which often requires grasping and holding the bone segments with forceps or similar instruments. This grasping entails intrusion of the grasping instrument around and behind the bones to be repositioned or held, which can damage tissue. For example, when performing a reduction on a rib, the grasping instruments violate the pleural cavity behind the rib segments, and the force required to manipulate the rib segments may also damage the ribs themselves.

To address these problems, a method and system for bone reduction and fixation is provided that is accomplished anteriorly, both in terms of manipulation of the bone segments and affixation of the bone plate, such that the need for grasping or encircling the bone segments is not required, thereby minimizing damage to the bones or the tissue surrounding the bones.

SUMMARY OF THE INVENTION

The method and the system for bone reduction and fixation of bone segments utilize a bone plate having a plurality of screw receiving apertures and a pair of elongated positioning or guide slots, each positioning slot being aligned with the reduction direction. Preferably the positioning slots are linearly aligned. A pair of elongated manipulating members each possessing an anchoring structure, such as a threaded screw structure on the distal end, are provided, preferably each with a removable drive grip or handle for easier control and rotation, whereby the anchoring structure may be driven or rotated into a bone segment. The anchoring structure and slots being sized such that the distal portion of the anchoring structures may be inserted through the positioning slots and secured to the bone segments by rotating or driving the manipulating member. Alternatively, the elongated manipulating member may temporarily mount onto independent bone fasteners, such as bone screws, adapted to be inserted through the positioning slots and into the bone segments.

In one embodiment, the bone plate is mounted to a first bone segment by positioning the bone plate on the first bone segment and attaching the first manipulating member to the first bone segment through a first positioning slot, then attaching the second manipulating member to the second bone segment through the second positioning slot. The anchoring structures of the manipulating members are not fully inserted into the bone segments, such that they do not secure the bone plate in fixed manner to the bone segments, instead allowing for relative movement between the bone plate and the bone segments and anchoring structures of the manipulating members The manipulating members are then slid within the slots so as to bring together or reposition the bone segments for proper alignment, at which time fixation bone screws are inserted through the screw receiving apertures into both bone segments to permanently affix the bone plate to the bone segments. The manipulating members are then removed.

In a second embodiment, the bone plate is first affixed to a first bone segment by inserting fixation bone screws through the screw receiving apertures. The first manipulating member is then mounted onto the first bone segment through the first positioning slot and the second manipulating member is mounted to the second bone segment through the second positioning slot. The bone segments are then properly repositioned by manipulation of the two manipulation members to move the bone segments relative to the bone plate. The bone plate is affixed to the second bone segment with additional fixation screws inserted through the screw receiving apertures, and the manipulating members are then removed.

In a third embodiment, the manipulating members are releasably connected to the anchoring structures, such that the anchoring structures may be first be driven into the bone segments through the positioning slots, with the manipulating members then joined to the anchoring members in order to reposition the bone segments. After fixation of the bone segments in the reduced alignment, the manipulating members are removed from the anchoring members, which are then removed from the bone segments are tightened onto the bone plate to serve as additional fixation members.

In these manners, bone segments separated by a gap may be repositioned, aligned and/or abutted such that the bone segments may regenerate into a single bone, or such that the segments are maintained in a fixed and structurally rigid configuration.

Alternatively summarized, the invention is a bone repositioning and fixation system adapted to reposition and affix two bone segments separated by a gap, said system comprising in combination: a bone plate comprising screw receiving apertures adapted to receive bone screws adapted to affix said bone plate to a first and second bone segment, said bone plate further comprising a first positioning slot and a second positioning slot, said first and second positioning slots being linearly aligned; a first manipulating member and a second manipulating member, each said manipulating member comprising a shaft and an anchoring structure connected to said shaft and adapted to temporarily affix said manipulating members to bone segments, wherein said anchoring members are sized and configured to be insertable through said positioning slots, and wherein said manipulating members or said anchoring members are movable longitudinally within said positioning slots relative to said bone plate; such that with said first manipulating member affixed to the first bone segment and with said second manipulating member affixed to the second bone segment, the bone segments may be brought together by moving said manipulating members together. In addition, such system wherein said first and second positioning slots are linear; wherein said manipulating members each comprise an elongated shaft and a handle; wherein said handles are removable from said shafts; wherein said anchoring members each comprise a tapered, threaded shaft; wherein said manipulating members each further comprise a shoulder positioned on said shaft, said shoulder sized and configured to prevent passage of said shoulder through said positioning slots; wherein said anchoring structures are detachable from said shafts; wherein each said anchoring structure comprises an internally threaded bore and each said shaft comprises an externally threaded post sized and configured to mate with said internally threaded bore; and/or wherein each said anchoring structure comprises a non-circular in cross-section bore and each said shaft comprises a non-circular in cross-section insertion post sized and configured to mate with said internally threaded bore; wherein each said anchoring structure comprises a head of greater width than said positioning slots.

Alternatively, a method of repositioning and affixing a first and second bone segment comprising the steps of: providing a bone reduction and fixation system adapted to reposition and affix two bone segments separated by a gap, said system comprising in combination: a bone plate comprising screw receiving apertures adapted to receive bone screws adapted to affix said bone plate to a first and second bone segment, said bone plate further comprising a first positioning slot and a second positioning slot, said first and second positioning slots being linearly aligned; a first manipulating member and a second manipulating member, each said manipulating member comprising a shaft and an anchoring structure connected to said shaft and adapted to temporarily affix said manipulating members to bone segments, wherein said anchoring members are sized and configured to be insertable through said positioning slots, and wherein said manipulating members or said anchoring members are movable longitudinally within said positioning slots relative to said bone plate; loosely affixing said bone plate to said first bone segment by inserting said anchoring structure of said first manipulating member through said first positioning slot and advancing said first manipulating anchoring member into said first bone segment and inserting said anchoring structure of said second manipulating member through said second positioning slot and advancing said second manipulating anchoring member into said second bone segment; moving said manipulating members toward each other within said positioning slots, such that said first and second bone segments are moved toward each other and repositioned; rigidly securing said bone plate to said repositioned bone segments by inserting bone screws through said screw receiving apertures; and removing said manipulating members from said bone segments. And further comprising the steps of providing said system wherein said anchoring structures comprise tapered threaded shafts; and wherein said step of loosely affixing said bone plate to said bone segments comprises rotationally driving said anchoring members into said bone segments; and/or providing said system wherein said anchoring structures are detachable from said shafts of said manipulating members and wherein said anchoring structures comprise heads of greater width than the width of said positioning slots; and after performing said step of rigidly securing said bone plate to said repositioned bone segments, said heads of said anchoring members are tightened against said bone plate and said shafts are detached from said anchoring structures.

Alternatively, a method of repositioning and affixing a first and second bone segment comprising the steps of: providing a bone reduction and fixation system adapted to reposition and affix two bone segments separated by a gap, said system comprising in combination: a bone plate comprising screw receiving apertures adapted to receive bone screws adapted to affix said bone plate to a first and second bone segment, said bone plate further comprising a first positioning slot and a second positioning slot, said first and second positioning slots being linearly aligned; a first manipulating member and a second manipulating member, each said manipulating member comprising a shaft and an anchoring structure connected to said shaft and adapted to temporarily affix said manipulating members to bone segments, wherein said anchoring members are sized and configured to be insertable through said positioning slots, and wherein said manipulating members or said anchoring members are movable longitudinally within said positioning slots relative to said bone plate; rigidly affixing said bone plate to said first bone segment by inserting bone screws through said screw receiving apertures and inserting said anchoring structure of said first manipulating member through said first positioning slot and advancing said first manipulating anchoring member into said first bone segment; loosely affixing said bone plate to said second bone segment by inserting said anchoring structure of said second manipulating member through said second positioning slot and advancing said second manipulating anchoring member into said second bone segment; moving said second manipulating member within said second positioning slot toward said first manipulating member, such that said first and second bone segments are moved toward each other and repositioned; rigidly securing said bone plate to said repositioned second bone segment by inserting bone screws through said screw receiving apertures; and removing said manipulating members from said bone segments. And further, providing said system wherein said anchoring structures comprise tapered threaded shafts; and wherein said step of affixing said bone plate to said bone segments comprises rotationally driving said anchoring members into said bone segments; and/or providing said system wherein said anchoring structures are detachable from said shafts of said manipulating members and wherein said anchoring structures comprise heads of greater width than the width of said positioning slots; and after performing said step of rigidly securing said bone plate to said repositioned bone segments, said heads of said anchoring members are tightened against said bone plate and said shafts are detached from said anchoring structures.

BRIEF DESCRIPTION OF THE DRAWINGS

FIG. 1 is a top view of a representative embodiment of the bone plate showing the pair of positioning slots and the screw receiving apertures.

FIG. 2 is an illustration of a representative embodiment of an anchoring mechanism for a manipulating member, the embodiment having a threaded tapered shaft.

DETAILED DESCRIPTION OF THE INVENTION

The figures accompanying this disclosure illustrate a bone plate 10 in the form of a rib plate, but it is to be understood that the illustrations are not meant to be limiting and bone plates 10 of varying configuration will be appropriate depending on the configuration of the bone segments 91/92 to be reduced, manipulated and fixated.

In general, the invention is a method and system for the reduction, manipulation and fixation of first and second bone segments 91/92, i.e., bones that have been divided into segments by fracture, degeneration, osteotomies or the like resulting in the presence of a gap or space 93 between the bone segments 91/92 that should be closed or minimized. The method and system provides a technique for bringing the bone segments 91/92 together to close the gap 93 whereby a bone plate 10 can then be affixed to the two bone segments 91/92 to maintain them in the repositioned arrangement. The technique minimizes damage to the bones and surrounding tissue.

Figure 3:
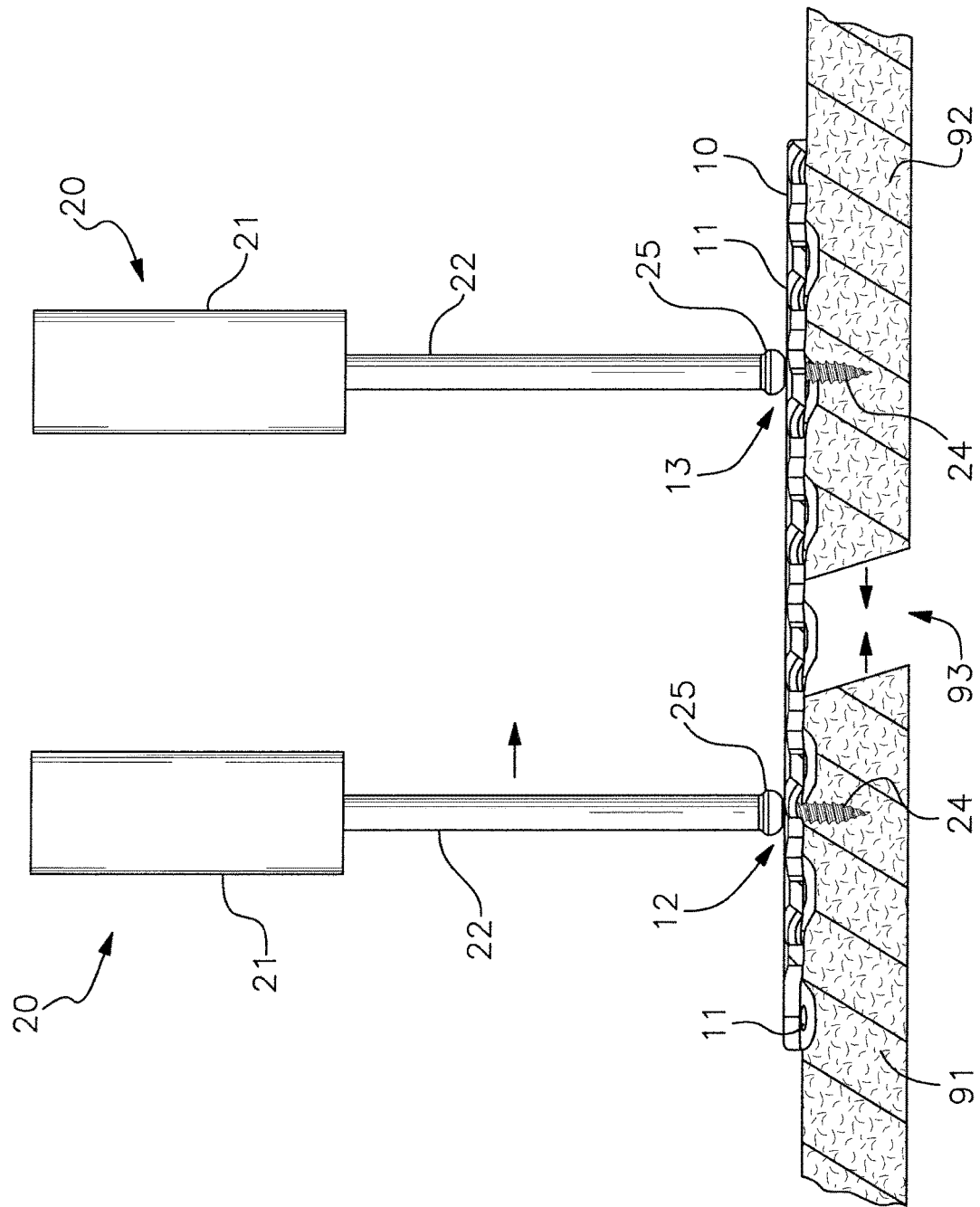
FIG. 3 is an illustration showing a pair of manipulating members inserted into the positioning slots and temporarily affixed to the bone segments, shown prior to bringing together the bone segments, the bone plate shown in cross-section along line 3-3 of FIG. 1.

The method and system utilize a bone plate 10 having a pair of linear, elongated, positioning or guide slots, shown as first and second positioning slots 12/13, and a plurality of screw receiving apertures 11. The positioning slots 12/13 are aligned in the direction over which reduction is to occur, and most preferably are linearly disposed such that the positioning slots 12/13 share a common longitudinal axis. For example, as shown in FIGS. 1 and 3, when a rib has been divided into bone segments 91/92 and it is desired to rejoin the rib, the line of reduction will be substantially coaxial for each bone segment 91/92 such that the two ends of the rib segments 91/92 need to be brought together, and therefore the two positioning slots 12/13 will be substantially linearly aligned. The length and width of the positioning slots 12/13 may vary depending on the configuration of the bone to be fixed and the amount of axial rotation that may be required for proper alignment. Most preferably the positioning slots 12/13 are evenly spaced along the bone plate 10.

A pair of elongated manipulating members 20 each having an anchoring structure 23 on the distal end are provided, as shown in FIG. 3. The manipulating member 20 comprises an elongated shaft 22 and most preferably a handle 21 to provide better gripping and control. The handles 21 may be removeable from the shafts 22. The manipulating member 20 is a driving tool, such that the manipulating member 20 may be rotated or forcibly driven to secure the anchoring structure 23 into a first bone segment 91 or a second bone segment 92.

The anchoring structure 23 on the distal end of each manipulating member 20 is configured so as to penetrate the bone segment 91/92. In the embodiment shown in FIGS. 2 and 3, the anchoring structure 23 comprises an externally threaded, tapered shaft, such that the anchoring structure 23 operates as a screw and may be rotated in a first direction to advance into the bone and rotated in a second direction for removal from the bone. The maximum width of the threaded portion is preferably chosen to be less than the width of the positioning slots 12/13 so that the anchoring structure can be driven into the bone a sufficient distance to provide a secure connection. The width or diameter of the shaft 22 may be smaller than the width of the positioning slots 12/13, or the width of the shaft 22 may be larger or a shoulder or flange 25 may be provided on the shaft 22 adjacent the anchoring structure 23 of the manipulating member 20, the width of the shoulder 25 preferably being greater than the width of the positioning slots 12/13 such that the shoulder 25 or shaft 22 is unable to pass into the positioning slots 12/13 and therefore precludes excessive forward travel of the manipulating member 20 into the bone segment 91/92. With this structure, the distal end of one of the manipulating members 20 is inserted into one of the positioning slots 12/13 and rotated to drive and temporarily affix the anchoring structure 23 of the manipulating member 20 into one of the bone segments 91/92. The manipulating members 20 are not tightly affixed against the bone segments 91/92 such that relative movement between the bone plate 10 and the bone segments 91/92 is still easily accomplished, the manipulating members 20 being easily moved longitudinally within the positioning slots 12/13 in order to reposition the bone segments 91/92.

Figure 4:
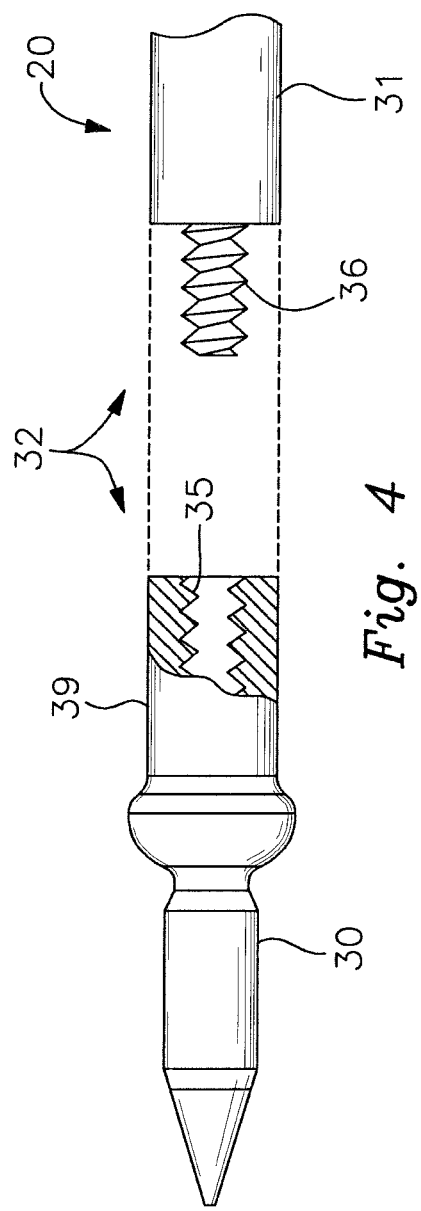
FIG. 4 is an illustration of another representative embodiment of an anchoring mechanism for a manipulating member, the embodiment having a bone fastener having a spike and an internally threaded bore which releasably mates with an externally threaded shaft disposed on the distal end of a manipulating member shaft.

In an alternative embodiment illustrated in FIG. 4, the anchoring structure 23 may comprise a point or spike 26. With this structure the spike 26 is driven into the bone by striking the proximal end of the manipulating member 20 with a hammer or similar tool.

Figure 5:
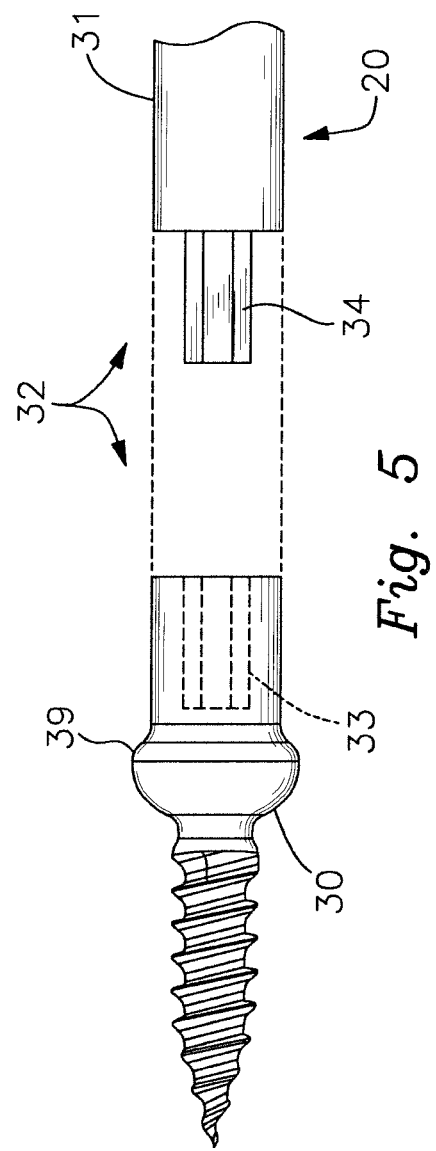
FIG. 5 is an illustration of another representative embodiment of an anchoring mechanism for a manipulating member, the embodiment having a bone fastener having a threaded tapered shaft and an internal bore which releasably mates with correspondingly shaped insert shaft disposed on the distal end of a manipulating member shaft.

Alternatively still, as shown in FIGS. 4 and 5, the elongated manipulating members 20 may comprise the combination of a shaft 31 and detachable anchoring members 23 comprising independent bone fasteners 30 adapted to be inserted through the positioning slots 12/13 and into the bone segments 91/92, the heads 39 of the bone fasteners 30 preferably being wider than the width of the positioning slots 12/13 so as to limit the amount of forward travel of the bone fastener 30 into the bone segment 91/92. As shown in FIG. 4, the anchoring structure bone fastener 30 may comprise a spike, or as shown in FIG. 5, the anchoring structure bone fastener 30 may comprise a tapered, threaded shaft. In the embodiment of FIG. 4, the proximal end of the bone fastener 30 is provided with an internally threaded bore 35 and the distal end of the manipulating member releasable shaft 31 is provided with a correspondingly sized and configured externally threaded post 36, the combination defining an engagement assembly 32, such that the manipulating member 20 may be rotationally joined and disconnected from the bone fastener 30. In the embodiment of FIG. 5, the proximal end of the bone fastener 30 is provided with a non-circular in cross-section (e.g., polygonal, star-shaped, etc.) bore 33 and the distal end of the releasable shaft 31 is provided with a correspondingly sized and configured non-circular in cross-section insertion post 34 to form the engagement assembly 32, such that the manipulating member 20 may be inserted and removed from the bone fastener 30, the non-circular configuration allowing rotational force to be applied to the bone fastener 30

With this structure it is possible, after manipulation and repositioning of the bone segments 91/92 into their desired configuration, to utilize the bone fasteners 30 located in the positioning slots 12/13 as additional fastening members securing the bone plate 10 to the bone segments 91/92 by driving the bone fasteners 30 further into the bone segments 91/92 and securely against the bone plate 10.

Figure 7:
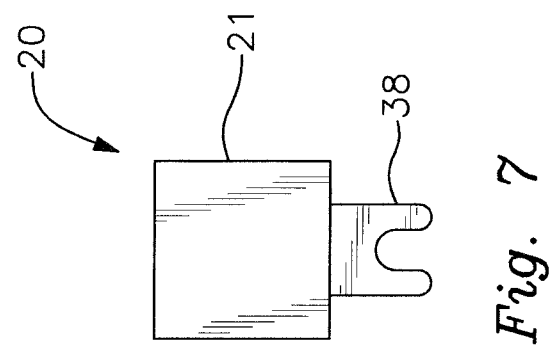
FIG. 7 is an illustration of an alternative embodiment for the engagement mechanism of a manipulating member shaft, the manipulating member shaft having slotted hook adapted to receive the head portion of a bone fastener.
Figure 6:
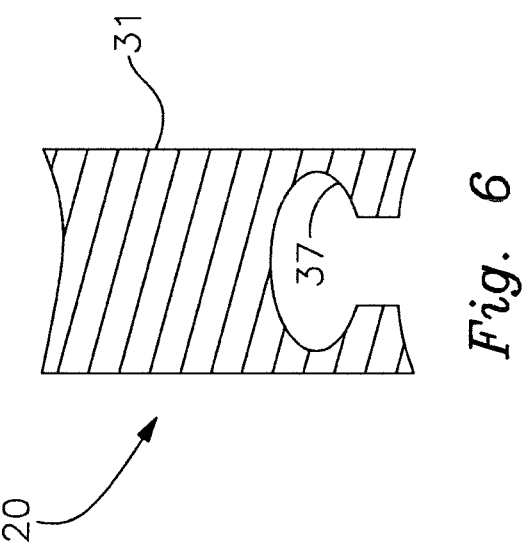
FIG. 6 is an illustration of an alternative embodiment for the engagement mechanism of a manipulating member shaft, the manipulating member shaft having a recess adapted to receive the head portion of a bone fastener.

Alternative embodiments for the distal ends of the releasable shaft 31 of the manipulating member 20 are shown in FIGS. 6 and 7. In FIG. 6, the distal end of the releasable shaft 31 is provided with a recess 37 open to the end and side of the shaft 31 and closed to the opposite side of the shaft 31, the recess 37 being sized and configured such that the manipulating member 20 can be laterally slid or positioned over the head 39 of the bone fastener 30. In FIG. 7, the distal end of the shaft 31 is provided with a laterally extending slotted hook member 37, the slotted hook member 37 being sized and configured such that it may be laterally slipped beneath the head 39 of the bone fastener 30. Both embodiments enable movement of the bone segments 91/92 relative to the bone plate 10.

In one embodiment of the method, the bone plate 10 is mounted to a first bone segment 91 by positioning the bone plate 10 on the first bone segment 91 and then attaching a first manipulating member 20 to the first bone segment 91 through a first positioning slot 12, i.e., the anchoring structure 23 on the distal end of the first manipulating member 20 is inserted into the first positioning slot 12 and the manipulating member 20 is then rotated or driven under forward pressure to drive the anchoring structure 23 into the first bone segment 91. Advancement of the manipulating member 20 is stopped at a point whereby the bone segment 91 is loosely connected and easily movable along the reduction direction relative to the bone plate 10, i.e., the manipulating member 10 is not used to press the bone plate 10 immovably against the bone segment 91. A second manipulating member 20 is then attached in similar manner to the second bone segment 92 through the second positioning slot 13. At this stage, the bone plate 10 is only loosely affixed to the bone segments 91/92 and the manipulating members 20 may be moved longitudinally within the positioning slots 12/13 to bring the bone segments 91/92 together, the positioning slots 12/13 controlling the direction of travel of the bone segments 91/92.

The manipulating members 20 are then grasped by the surgeon and used as anteriorly-extending handles to bring together or reposition the bone segments 91/92 relative to each other for proper alignment, thereby closing the gap 93 that previously existed. Grasping instruments are not required to move the bone segments 91/92, as movement of the manipulating members 20 toward each other results in movement of the bone segments 91/92 toward each other. With this system, manipulation of the bone segments 91/92 occurs anteriorly, the manipulating members 20 extending outwardly from the bone plate 10 and bone segments 91/92 so as to provide an easily grasped structure.

With the bone segments 91/92 properly repositioned, fixation bone screws (not shown) are now inserted through the screw receiving apertures 11 of the bone plate 10 into both bone segments 91/92 such that the bone plate 10 is securely and rigidly affixed to the bone segments 91/92 and the bone segments 91/92 are secured in the desired post-operative position relative to each other. The manipulating members 20 are then removed by pulling or reversing the rotation to back out the anchoring structures 23 from the bone segments 91/92.

In a second embodiment of the method, the bone plate 10 is first affixed to a first bone segment 91 by inserting fixation bone screws (not shown) through some of the screw receiving apertures 11. The first manipulating member 20 is then mounted onto the first bone segment 91 through the first positioning slot 12 and the second manipulating member 20 is mounted to the second bone segment 92 through the second positioning slot 13. The bone segments 91/92 are then properly repositioned by manipulation of the two manipulation members 20. The bone plate 10 is then affixed to the second bone segment 92 with additional fixation bone screws inserted through the screw receiving apertures 11, and the manipulating members 20 are then removed.

In a third embodiment of the method utilizing bone fasteners 30 independent and separate from the manipulating member 20, the two being joined by an engagement assembly 32, the bone fasteners 30 are affixed to the bone segments 91/92, either with a separate driving tool (such as with the configurations of FIGS. 6 and 7) or with the releasable shaft manipulating member 20 itself (as in FIGS. 4 and 5). The bone segments 91/92 are repositioned and securely affixed with fixation bone screws inserted through the screw receiving apertures 11. The manipulating members 20 are then used to tighten the bone fasteners 30 onto the bone plate 10, and then disconnected from the bones fasteners 30, such that the bone fasteners 30 act as additional fixation members.

It is understood that equivalents for equivalents and substitutions for steps and elements set forth above may be obvious to those of ordinary skill in the art, and therefore the true scope and definition of the invention is to be as set forth in the following claims.

We claim:

1. A bone repositioning and fixation system adapted to reposition and affix two bone segments separated by a gap, said system comprising in combination:
   a bone plate comprising screw receiving apertures adapted to receive bone screws adapted to affix said bone plate to a first and second bone segment, said bone plate further comprising a first positioning slot and a second positioning slot, said first and second positioning slots each having a maximum width and being linearly aligned;
   a first manipulating member and a second manipulating member, each said manipulating member comprising a shaft and an anchoring structure non-removably connected to said shaft and adapted to temporarily affix said manipulating members to bone segments, wherein said anchoring structures are sized and configured to be insertable through said positioning slots, and wherein said manipulating members or said anchoring structures are movable longitudinally within said positioning slots relative to said bone plate;
   wherein said manipulating members each further comprise a shoulder positioned on said shaft adjacent said anchoring structures, said shoulder having a minimum diameter larger than said maximum width of each of said positioning slots to prevent passage of said shoulder through said positioning slots;
   such that with said first manipulating member affixed to the first bone segment and with said second manipulating member affixed to the second bone segment, the bone segments may be brought together by moving said manipulating members together, such that upon inserting said bone screws through said screw receiving apertures in said bone segments, said bone segments remain in fixed relation when said manipulating members are removed from said bone segments.

2. The system of claim 1, wherein said first and second positioning slots are linear.

3. The system of claim 1, wherein said manipulating members each comprise an elongated shaft and a handle.

4. The system of claim 1, wherein said anchoring structures each comprise a tapered, threaded shaft.

5. A bone repositioning and fixation system adapted to reposition and affix two bone segments separated by a gap, said system comprising in combination:
   a bone plate comprising screw receiving apertures adapted to receive bone screws adapted to affix said bone plate to a first and second bone segment, said bone plate further comprising a first positioning slot and a second positioning slot, said first and second positioning slots each having a maximum width and being linearly aligned;

a first manipulating member and a second manipulating member, each said manipulating member comprising a shaft having a diameter or width and an anchoring structure non-removably connected to said shaft and adapted to temporarily affix said manipulating members to bone segments, wherein said anchoring structures are sized and configured to be insertable through said positioning slots, and wherein said manipulating members or said anchoring structures are movable longitudinally within said positioning slots relative to said bone plate;

wherein said diameter or width of each said shaft adjacent said anchoring structure is larger than said maximum width of each of said positioning slots to prevent passage of said shaft through said positioning slots;

such that with said first manipulating member affixed to the first bone segment and with said second manipulating member affixed to the second bone segment, the bone segments may be brought together by moving said manipulating members together, such that upon inserting said bone screws through said screw receiving apertures in said bone segments, said bone segments remain in fixed relation when said manipulating members are removed from said bone segments.

6. The system of claim 5, wherein said first and second positioning slots are linear.

7. The system of claim 5, wherein said manipulating members each comprise an elongated shaft and a handle.

8. The system of claim 5, wherein said anchoring structures each comprise a tapered, threaded shaft.

\* \* \* \* \*